United States Patent [19]
Takeuchi

[11] Patent Number: 5,848,968
[45] Date of Patent: Dec. 15, 1998

[54] ULTRASONIC IMAGING METHOD AND APPARATUS

[75] Inventor: Yasuhito Takeuchi, Tokyo, Japan

[73] Assignee: GE Yokogawa Medical Systems, Limited, Tokyo, Japan

[21] Appl. No.: 874,549

[22] Filed: Jun. 13, 1997

[30] Foreign Application Priority Data

Jun. 19, 1996 [JP] Japan .................................. 8-157941

[51] Int. Cl.⁶ .............................................. A61B 08/00
[52] U.S. Cl. ......................................................... 600/458
[58] Field of Search ................................... 600/458, 442

[56] References Cited

U.S. PATENT DOCUMENTS

| | | | |
|---|---|---|---|
| 4,276,885 | 7/1981 | Tickner et al. ......................... | 600/458 |
| 4,572,203 | 2/1986 | Feinstein ................................ | 600/458 |
| 5,302,372 | 4/1994 | Lin et al. ................................ | 600/458 |
| 5,456,257 | 10/1995 | Johnson et al. ........................ | 600/458 |
| 5,487,390 | 1/1996 | Cohen et al. .......................... | 600/458 |

*Primary Examiner*—Marvin M. Lateef
*Assistant Examiner*—Maulin Patel
*Attorney, Agent, or Firm*—Moonray Kojima

[57] ABSTRACT

An ultrasonic imaging apparatus devised to implement contrast imaging of enhanced S/N ratios. The apparatus comprises: an exciting unit for generating ultrasonic waves by stimulating a contrast medium introduced into a target object; a contrast image creating unit for creating a contrast image based on the ultrasonic waves generated through stimulation; an echo generating unit for generating echoes of the ultrasonic waves transmitted into the target object; an echo image creating unit for creating an echo image based on the generated echoes; and a display unit for superimposing the contrast image and the echo image for display.

24 Claims, 2 Drawing Sheets

ULTRASONIC IMAGING METHOD AND APPARATUS

BACKGROUND OF THE INVENTION

1. Field of the Invention

The present invention relates to a method and an apparatus capable of ultrasonic imaging with an enhanced S/N (signal-to-noise) ratio.

2. Description of the Related Art

Ultrasonic imaging systems transmit ultrasonic pulses to a target object, receive echoes of the pulses and get an image of the interior of the target object based on the echo data. Ultrasonic pulses are transmitted and received in the form of directional beams. Using beam-type transmission and reception of ultrasonic waves, an ultrasonic probe scans a desired region inside the target object (i.e., imaging area) to acquire sufficient echo data for generating a desired image.

Experience has shown that to achieve B-mode imaging with a good S/N ratio requires setting at least to ±1 Mpa (megapascal) the irradiation level of ultrasonic pulses (i.e., instantaneous sound pressure) especially in the vicinity of an ultrasonic focus.

One way of carrying out ultrasonic imaging involves the use of a contrast medium. The contrast medium is typically composed of micro-balloons or micro-bubbles. The micro-balloon-based contrast medium is offered in a liquid form with infinitesimal air bubbles (about 2 to 10 $\mu$m across each) mixed therein.

When their diameter resonates with a specific ultrasonic frequency, micro-balloons manifest a nonlinear ultrasonic reflection characteristic that is dependent on the instantaneous sound pressure in effect. The nonlinear ultrasonic reflection characteristic in turn produces echoes including second harmonics of the irradiated ultrasonic beam. Such echoes are utilized in imaging the target portion into which the contrast medium has been introduced.

For successful imaging by use of the micro-balloon-based contrast medium, it is necessary to irradiate an ultrasonic beam whose sound level must not be high enough to destroy any micro-balloons. This requires that the instantaneous sound level of ultrasonic irradiation be illustratively within about ±50 KPa.

That ultrasonic irradiation level is about one twentieth of the commonly used irradiation level for ordinary B-mode imaging, the latter ordinary level being about ±1 MPa. In terms of irradiation power, the level of ultrasonic irradiation involving the use of the micro-balloon-based contrast medium is as low as one four-hundredth of the power level of B-mode imaging.

Ultrasonic images obtained with such feeble power have S/N ratios so poor that the image quality is manifestly inferior.

SUMMARY OF THE INVENTION

It is therefore an object of the present invention to provide a method and an apparatus for ultrasonic imaging enabling images to be obtained with an improved S/N ratio where a micro-balloon-based contrast medium is used.

In carrying out the invention and according to a first aspect thereof, there is provided an ultrasonic imaging method comprising the steps of: generating ultrasonic waves by stimulating a contrast medium introduced into a target object; creating a contrast image based on the ultrasonic waves thus generated; producing an echo image based on echoes of the ultrasonic waves transmitted into the target object; and superimposing the contrast image and the echo image for display.

The inventive method above is characterized in that the contrast medium introduced into the target object is stimulated to produce ultrasonic waves which in turn are used as the basis for generating the contrast image. The contrast image has an enhanced S/N ratio because it is produced on the basis of high-level ultrasonic waves. When superimposed onto the echo image, the contrast image provides clear indications of correlations with the surroundings of the imaged target.

According to a second aspect of the invention, there is provided an ultrasonic imaging apparatus comprising:
  excitation means for generating ultrasonic waves by stimulating a contrast medium introduced into a target object;
  contrast image creation means for creating a contrast image based on the ultrasonic waves generated through stimulation by the excitation means; echo generation means for generating echoes of the ultrasonic waves transmitted into the target object; echo image creation means for creating an echo image based on the echoes generated by the echo generation means;
  and display means for superimposing the contrast image and the echo image for display.

The inventive apparatus above stimulates the contrast medium introduced into the target object to generate ultrasonic waves which in turn are used to generate the contrast image. This allows the contrast image to be generated on the basis of high-level ultrasonic waves, whereby contrast imaging with an enhanced S/N ratio is implemented. When superimposed onto the echo image, the contrast image likewise manifests clear indications of correlations with the surroundings of the imaged target.

According to a third aspect of the invention, there is provided an ultrasonic imaging apparatus comprising:
  excitation means for causing particles of an explosive substance introduced into a target object to explode through ultrasonic stimulation; and image creation means for creating an image based on the ultrasonic waves generated by explosion of the particles.

According to a fourth aspect of the invention, there is provided a contrast medium composed of a liquid mixed with particles of an explosive substance.

The additional above aspects of the invention are characterized in that high-level ultrasonic waves are generated by causing particles of an explosive substance to explode through ultrasonic stimulation. The inventive contrast medium capable of generating such high-level ultrasonic waves enables contrast imaging to be conducted with an enhanced S/N ratio. Preferably, the particles should be bubbles of a hydrogen and oxygen mixture because they turn into harmless water after explosion.

Further objects and advantages of the present invention will be apparent from the following description of the preferred embodiments of the invention as illustrated in the accompanying drawings.

DESCRIPTION OF THE PREFERRED EMBODIMENTS

Contrast Medium

Figure 1:
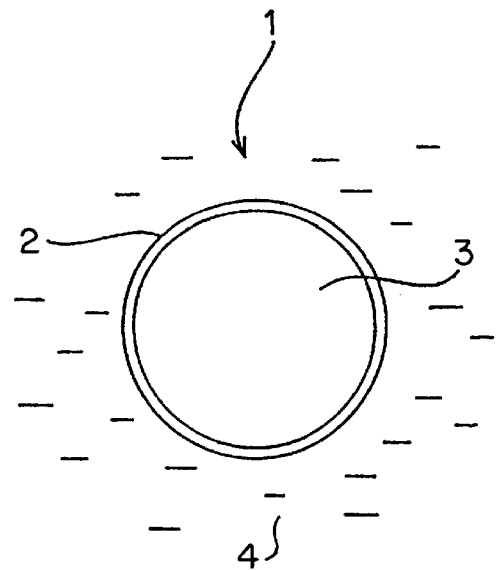
FIG. 1 is a conceptual view of a typical contrast medium embodying the invention.

FIG. 1 is a conceptual view of a typical contrast medium practiced as an embodiment of the invention. As depicted in FIG. 1, the contrast medium is composed of micro-balloons 1 mixed in a water solution 4. The diameter of each micro-balloon may illustratively be 2 to 20 $\mu$m small enough for the micro-balloons to pass through capillaries.

Micro-balloons 1 are each constituted by a capsule 2 containing a sound generating agent 3 inside. The capsule 2 is typically mad e of a surface-active agent film. The surface-active agent is selected preferably from among a dexistran water solution, a sodium laurate water solution and a saponin water solution, because any one of these substances has a long film life and proves to be harmless to organisms.

The sound generating agent 3 is constituted by a substance that generates ultrasonic waves when physically stimulated from the outside.

One such substance is an explosive. A typical explosive is a so-called detonating gas that has hydrogen gas (H2) and oxygen gas (O2) mixed in suitable proportions. The detonating gas is preferred as an explosive because it turns into water that is harmless to organisms after explosion.

Alternatively, a mixture of a fuel gas such as methane or propane with oxygen gas, or an explosive such as nitroglycerin (in liquid form) or lead azide (in solid form) may be utilized depending on the object of imaging.

The contrast medium using gas as an explosive is prepared illustratively as follows: a mixture of a dexistran water solution or the like and an explosive gas (detonating gas, gas mixture, etc.) of a suitable proportion is put into a closed vessel and stirred. The resulting mixture is excited by ultrasonic waves at about tens of KHz. The excitation produces numerous micro-balloons within the dexistran water solution. The micro-balloons contain explosive gas each. For actual use, the micro-balloon-filled dexistran water solution is diluted as needed.

The micro-balloon-filled contrast medium comprising a liquid or a solid explosive may be prepared where necessary through the use of known micro-balloon encapsulation techniques.

When a contrast image needs to be acquired, explosive-filled micro-balloons are first introduced into the target object. Ultrasonic waves are then irradiated externally to the target object to destroy the micro-balloons residing inside. To be sufficient in performance, such ultrasonic waves need only have an instantaneous sound pressure of 50 to 100 KPa inside the target object. Destroying the micro-balloons ignites the explosive substance through compression in the same process as cavitation.

The explosion generates ultrasonic waves that act as signals indicating the presence of the detonated micro-balloons. These ultrasonic waves are of appreciably wideband nature possessing far greater energy than those irradiated to the micro-balloons. That is, the contrast medium reflects the irradiated ultrasonic waves through amplification, i.e., the medium returns wideband echoes having a gain.

Using the above type of contrast medium permits contrast imaging of a highly enhanced S/N ratio. In applications where the traditionally experienced S/N ratio is tolerated, contrast imaging using the inventive contrast medium will cover target regions much farther (i.e., deeper) than those addressed by conventional schemes.

Conventional micro-balloon-based contrast media also generate ultrasonic waves when their micro-balloons are destroyed in what is known as "StAE" (stimulated acoustic emission). However, the energy released from conventional micro-balloons does not exceed the energy level accumulated in a single ultrasonic wave cycle immediately before destruction. Unlike the contrast medium according to the invention, there has been no way of generating amplified ultrasonic waves. That is, conventional schemes have failed to produce high-level echoes that are characteristic of the inventive contrast medium.

Figure 2:
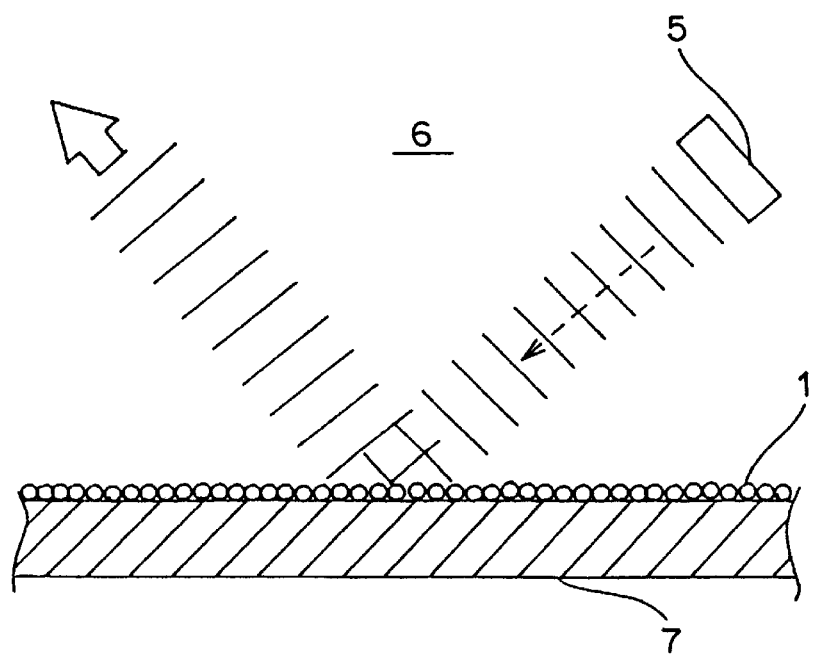
FIG. 2 is a schematic view of an applied setup in which the contrast medium of the invention illustratively works.

A setup in which the micro-balloon-based contrast medium is effectively utilized may be an ultrasonic intensifier 6 shown in FIG. 2. The ultrasonic intensifier 6 involves having the surface of a plate 7 covered with a layer of micro-balloons 1 as illustrated.

In operation, an ultrasonic irradiator 5 irradiates ultrasonic waves onto the surface of the ultrasonic intensifier 6. The irradiation causes micro-balloons 1 to explode, generating ultrasonic waves higher in level than the irradiated ultrasonic waves. That is, the setup works as a device to amplify and reflect the irradiated ultrasonic waves.

When the plate 7 is shaped flat as shown, the component acts as a plane mirror capable of ultrasonic wave amplification. If the plate 7 has a concave surface, the component works as a concave mirror capable of ultrasonic amplification; if the plate 7 has a convex surface, the component acts as a convex mirror also capable of ultrasonic amplification. The plate 7 may be suitably shaped as needed.

The sound generating agent 3 that generates ultrasonic waves when physically stimulated from the outside is not limited to explosives. Alternatively, the sound generating agent 3 may be a magnetic substance such as ferrite which generates ultrasonic waves through magneto-striction triggered by magnetic stimulation, or a loss-type dielectric substance that generates ultrasonic waves through expansion caused by electromagnetic wave overheating. Any one of such alternative sound generating agents can generate ultrasonic waves higher in level than the conventional micro-balloon-based contrast medium StAE.

Ultrasonic Imaging Apparatus

Figure 3:
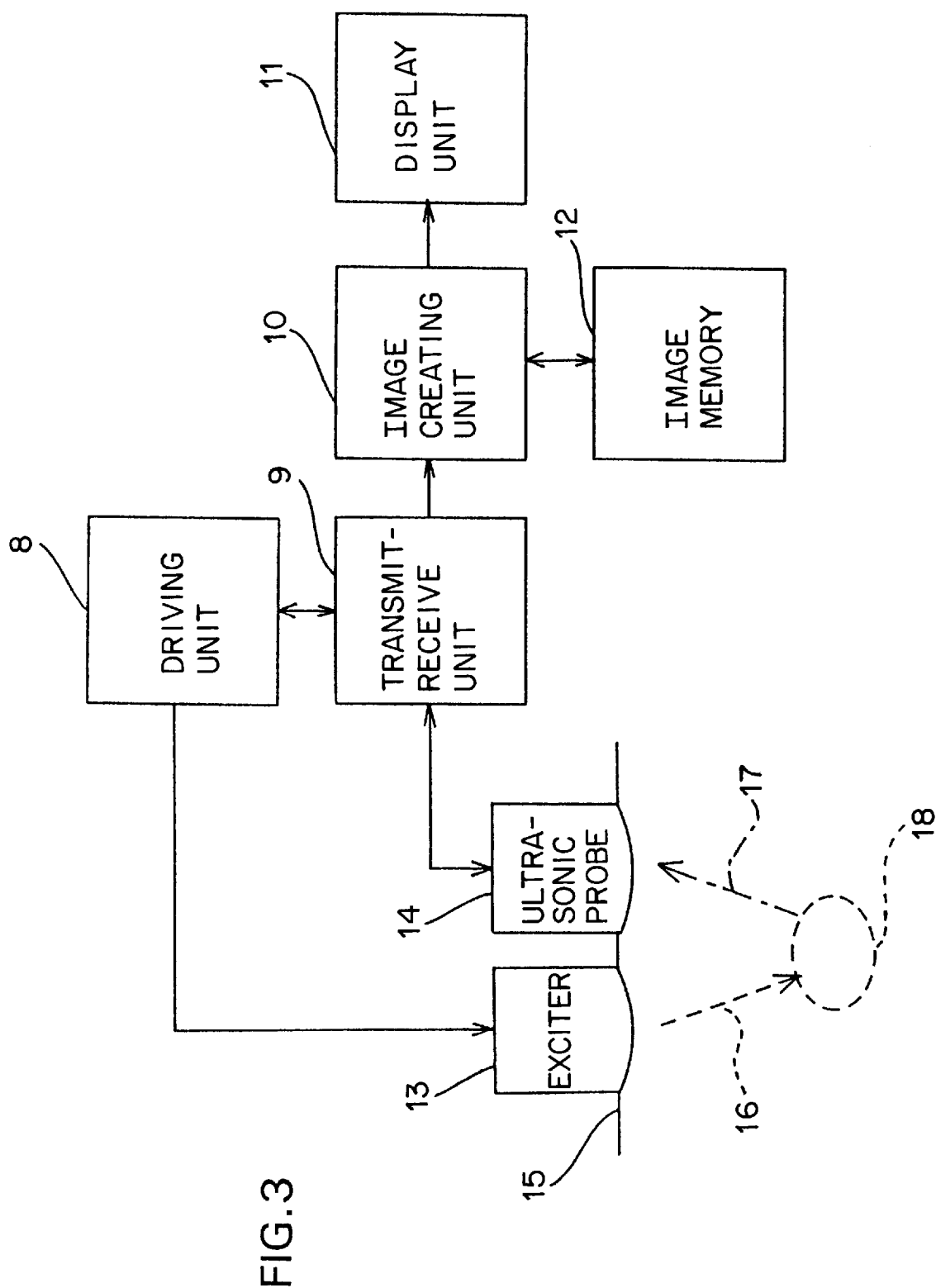
FIG. 3 is a block diagram of an apparatus also embodying the invention.

FIG. 3 is a block diagram of an ultrasonic imaging apparatus also embodying the invention. The constitution of this apparatus is indicated as a physical embodiment of the present invention; the workings of the apparatus are presented below as a procedural embodiment of the invention.

As shown in FIG. 3, a region of interest 18 which forms contrasts is located inside the target object 15. The contrast-forming region 18 is a region such as a blood-flowing portion into which the contrast medium has been introduced.

An exciter 13 located outside the body applies stimulation 16 to the contrast medium in the target object 15. The exciter 13 is driven by a driving unit 8.

The type of the exciter 13 corresponds to the kind of contrast medium in use. Specifically, an ultrasonic irradiating exciter is used in combination with explosive-filled micro-balloons; a magnetic pulse generating exciter is employed in conjunction with a magnetic substance-based contrast medium; a microwave emitting exciter is utilized where a dielectric substance-based contrast medium is used.

An ultrasonic probe 14 transmits ultrasonic waves into the target object 15 to generate and receive echoes therefrom. In addition, the ultrasonic probe 14 receives ultrasonic waves 17 generated by the contrast medium in the region of interest 18.

The ultrasonic probe 14 illustratively has an array of numerous ultrasonic oscillators, not shown. The ultrasonic oscillator array may be of one-dimensional, two-dimensional, or any other type depending on the purpose of imaging.

A transmitting-receiving unit 9 controls the ultrasonic probe 14 to transmit and receive ultrasonic waves. This makes it possible illustratively to scan the interior of the target object OBJ sequentially with an ultrasonic beam and to collect echo data successively therefrom. Receive data about the ultrasonic waves arriving from the region of interest 18 may also be gathered consecutively in the same sequence in which the ultrasonic beam is applied.

An explosive-based contrast medium, when used, may alternatively be stimulated by ultrasonic emissions from the ultrasonic probe 14. This setup is preferred because it eliminates the need for the exciter 13 and driving unit 8.

An image creating unit 10 creates images about the interior of the target object 15 on the basis of the echo data or ultrasonic receive data collected by the transmitting-receiving unit 9.

Images created by the image creating unit 10 are stored in an image memory 12. The images are also displayed on a display unit 11.

Contrast Imaging

Contrast-based imaging is carried illustratively as follows: an echo image is first taken of the inside of the target object 15 with no contrast medium introduced thereinto. The ultrasonic probe 14 is illustratively used to scan the interior of the target object 15 with an ultrasonic beam in order to collect echo data. The collected echo data is used by the image creating unit 10 in creating an echo image. The echo image thus created is placed in the image memory 12 and also displayed on the display unit DIS.

Next, the contrast medium of the above-described composition is introduced into the target object 15. It is assumed here that the contrast medium of micro-balloons filled with detonating gas is utilized. That is, the sound generating agent 3 shown in FIG. 1 is assumed to be detonating gas. After the contrast medium is deemed to have spread throughout the region of interest 18, the same region previously subjected to echo imaging is now exposed to contrast imaging.

When not destroyed, the contrast medium of detonating gas-filled micro-balloons permits imaging of second harmonics, i.e., the same kind as that of conventional schemes. As needed, the region of interest is scanned with an ultrasonic beam not strong enough to destroy the micro-balloons (i.e., instantaneous sound pressure being not in excess of 50 KPa in the region of interest 18), whereby echo data based on second harmonics is collected. The echo data thus gathered is used as the basis for generating a contrast image of the region of interest 18.

The contrast image is displayed on the display unit 11 for observation of the region of interest 19. At this point, the echo image taken before introduction of the contrast medium may be retrieved from the image memory 12 and superimposed onto the contrast image. This procedure offers a display of the target object with a clear indication of its relations to the surrounding tissues. Although the contrast image obtained here has a poor S/N ratio, the process is significant in that it provides the same contrast imaging as conventional schemes.

When contrast imaging of an enhanced S/N ratio is to be carried out, the sound pressure of the ultrasonic beam is boosted for scanning. In this case, the instantaneous sound pressure of the ultrasonic beam in the region of interest 18 is raised to a level high enough (e.g., 100 KPa or higher) to destroy the applied micro-balloons. This sound pressure is appreciably lower than that of B-mode imaging (typically 1 MPa) and is thus easy to output.

The process above causes the micro-balloons in the region of interest 18 to explode, releasing high-level ultrasonic waves, i.e., high-level echoes. The echo data is collected by the transmitting-receiving unit 9 via the ultrasonic probe 14. The gathered echo data is used by the image creating unit 10 in creating a contrast image, i.e., an image showing how ultrasonic wave generating sources are distributed in the target region. The echo data has an enhanced S/N ratio because the levels of the echoes are high. As a result, the contrast image created in the process above also has an improved S/N ratio.

Since the micro-balloons in the range of imaging explode and disappear upon every scan of the ultrasonic beam, each scan of the beam is followed by a predetermined elapse of time before the next scan may commence. The interval between beam scans is a period of time in which a necessary and sufficient amount of contrast medium is introduced anew into the region of interest 18.

The contrast image thus obtained is stored into the image memory 12. The image is retrieved repeatedly from memory for display on the display unit 11 before a new contrast image is created. During the repeated display, the echo image in effect prior to the introduction of the contrast medium is also displayed in a superimposed format. The process makes it possible to observe the target object in a contrast image of an enhanced S/N ratio giving a clear indication of the relations of the object to the surrounding tissues.

Instead of the ultrasonic probe 14, a dedicated exciter 13 generating ultrasonic pulses may be used alternatively to stimulate micro-balloons. This setup is preferred because the dedicated component applies optimum stimulation to the micro-balloons independently of the ultrasonic probe 14.

Where the contrast medium to be used comprises a magnetic substance-based sound generating agent 3, an exciter 13 generating magnetic pulses is employed. The exciter 13 emits magnetic pulses into the target object 15. In response, the sound generating agent 3 oscillates through magneto-striction, generating ultrasonic waves.

The ultrasonic waves thus generated are received by the ultrasonic probe 14. The resulting ultrasonic receive data is collected by the transmitting-receiving unit 9 via the ultrasonic probe 14. The collected data is used by the image creating unit 10 in creating a contrast image, i.e., an image showing how ultrasonic wave generating sources are distributed in the target region. This image is also displayed on the display unit 11 in the same manner as in the above-described process.

High-level ultrasonic waves may be generated by suitably establishing the intensity of pulse fields. This provides ultrasonic data of an enhanced S/N ratio, whereby contrast images of good S/N ratios are readily obtained.

Unlike the detonating gas-based contrast medium, the contrast medium comprising the magnetic substance-based sound generating agent does not disappear every time the agent generates ultrasonic waves. It follows that stimulation may be repeated at short intervals to trigger ultrasonic waves with no need to wait for the introduction of a further contrast medium. Because the contrast medium is not destroyed by ultrasonic waves, the ultrasonic probe 14 may transmit and receive ultrasonic waves so as to acquire echo images concurrently with the ongoing contrast imaging process.

Where the contrast image to be used comprises a dielectric substance-based sound generating agent 3, an exciter 13 generating microwaves is employed. The exciter 13 emits microwaves into the target object 15. In turn, the sound generating agent 3 heats up through dielectric loss and expands, generating microwaves or ultrasonic waves.

The ultrasonic waves thus generated are received by the ultrasonic probe 14. The resulting ultrasonic receive data is collected by the transmitting-receiving unit 9 via the ultrasonic probe 14. The collected data is used by the image creating unit 10 in creating a contrast image, i.e., an image showing how ultrasonic wave generating sources are distributed in the target region. This image is also displayed on the display unit 11 in the same manner as described earlier.

High-level ultrasonic waves may also be generated by suitably establishing the intensity of microwaves. This provides ultrasonic data of an enhanced S/N ratio, whereby contrast images of good S/N ratios are readily acquired.

As with the contrast medium comprising the magnetic substance-based sound generating agent, the contrast medium made of the dielectric substance-based sound generating agent does not disappear every time the agent generates ultrasonic waves. Stimulation may be repeated at short intervals to trigger ultrasonic waves with no need to wait for the introduction of a further contrast medium. Because the contrast medium is not destroyed by ultrasonic waves, the ultrasonic probe 14 may transmit and receive ultrasonic waves to acquire echo images concurrently with the ongoing contrast imaging process.

When the images thus obtained are appropriately positioned and superimposed on the display screen, both the contrast image and the echo image may be displayed in real time. In such a case, it is preferable that the echo and contrast images be written to a frame memory (not shown) in the display unit 11 at twice the frame rate in effect; the procedure raises the frame rate for image display. It is also preferred to color the contrast image for easy identification.

Echo imaging and contrast imaging may both be implemented through ultrasonic holography. Alternatively, the two kinds of imaging may be practiced through diffraction tomography.

Echo imaging and contrast imaging may be multiplexed either on a time division basis, or by frequency division through ultrasonic frequency differentiation. Where energy-dispersed ultrasonic imaging is implemented through the use of coded phase-modulated (or frequency-modulated) ultrasonic waves, echo imaging and contrast imaging may be multiplexed through code differentiation (i.e., code division).

Many widely different embodiments of the invention may be constructed without departing from the spirit and the scope of the present invention. It should be understood that the present invention is not limited to the specific embodiments described in the specification, except as defined in the appended claims.

What is claimed is:

1. An ultrasonic imaging method comprising the steps of:
   introducing into a target object a contrasting medium comprising a sound generating agent within a microbubble;
   generating ultrasonic waves by stimulating said contrasting medium to cause said sound generating agent to generate a unique ultrasonic wave different from ultrasonic waves caused by said target object;
   creating a contrast image based on the ultrasonic waves generated when said sound generating agent is activated;
   producing an echo image based on echoes of ultrasonic waves applied to said target object; and
   superimposing said contrast image and said echo image for display.

2. The method of claim 1, wherein said sound generating agent is an explosive substance.

3. The method of claim 2, wherein said explosive substance consists of hydrogen and oxygen.

4. The method of claim 2, wherein said explosive substance comprises a mixture of propane and oxygen.

5. The method of claim 2, wherein said explosive substance comprises a mixture of propane and oxygen.

6. The method of claim 2, wherein said explosive substance comprises lead azide in solid form.

7. The method of claim 2, wherein said explosive substance comprises nitroglycerine in liquid form.

8. The method of claim 1, wherein said sound generating agent comprises a magnetic substance, and wherein said contrasting medium generates an ultrasonic wave by magneto-striction of said magnetic substance caused by application of a magnetic field.

9. The method of claim 8, wherein said magnetic substance comprises ferrite.

10. The method of claim 1, wherein said sound generating agent comprises a dielectric, and wherein said contrasting medium generates an ultrasonic wave by expansion of said dielectric caused by application of an electric field to heat said diectric.

11. The method of claim 1, wherein said microbubbles are between 2 to 20 $\mu$m in size, and comprises a surface active agent selected from the group consisting of dextran water solution, sodium laurate water solution, and saponin water solution.

12. The method of claim 2, wherein said ultrasonic waves have an instantaneous sound pressure inside said target object of between 50 to 100 KPa, wherein said explosive substance is ignited through compression, and wherein said ultrasonic waves generated by explosion of said explosive substance has a wide band and produces high level echoes.

13. An ultrasonic imaging apparatus comprising:
   means for introducing into a target object a contrasting medium comprising a sound generating agent contained within a microbubble;
   excitation means for generating ultrasonic waves by stimulating said contrasting medium to thereby cause said sound generating agent to be activated;
   contrast image creating means for creating a contrast image based on said ultrasonic waves generated by activation of said sound generating agent;
   echo generating means for generating echoes of ultrasonic waves applied to said target object;
   echo image creating means for creating an echo image based on said echoes generated by said echo generating means; and
   display means for superimposing said contrast image and said echo image.

14. The apparatus of claim 13, wherein said sound generating agent is an explosive substance.

15. The apparatus of claim 14, wherein said explosive substance consists of hydrogen and oxygen.

16. The apparatus of claim 14, wherein said explosive substance comprises a mixture of propane and oxygen.

17. The apparatus of claim 14, wherein said explosive stance comprises a mixture of propane and oxygen.

18. The apparatus of claim 14, wherein said explosive substance comprises lead azide in solid form.

19. The apparatus of claim 14, wherein said explisive substance comprises nitroglycerine in liquid form.

20. The apparatus of claim 13, wherein said sound generating agent comprises a magnetic substance, and wherein said excitation means comprises means for applying a magnetic field to cause said contrasting medium to generate an ultrasonic wave by magneto-striction of said magnetic substance.

21. The apparatus of claim 20, wherein said magnetic substance comprises ferrite.

22. The apparatus of claim 13, wherein said sound generating agent comprises a dielectric, and wherein said excitation means comprises means for applying an electric field to cause said contrasting medium to generate an ultrasonic wave by expansion of said dielectric.

23. The apparatus of claim 13, wherein said microbubbles are between 2 to 20 $\mu$m in size, and comprises a surface active agent selected from the group consisting of dextran water solution sodium laurate water solution, and saponin water solution.

24. The apparatus of claim 14, wherein said ultrasonic waves have an instantaneous sound pressure inside said target object of between 50 to 100 KPa, wherein said explosive substance is ignited through compression, and wherein said ultrasonic waves generated by explosion of said explosive substance has a wide band and produces high level echoes.

* * * * *